United States Patent [19]
Patel et al.

[11] Patent Number: 5,215,886
[45] Date of Patent: * Jun. 1, 1993

[54] HDL DETERMINATION IN WHOLE BLOOD

[76] Inventors: P. Jivan Patel, 1235 Wildwood Ave. (#102), Sunnyvale, Calif. 94089; Michael P. Allen, 677 W. Garland Ter., Sunnyvale, Calif. 94086; Prithipal Singh, 25627 Elena Rd., Los Altos Hills, Calif. 94022

[*] Notice: The portion of the term of this patent subsequent to Sep. 25, 2007 has been disclaimed.

[21] Appl. No.: 616,628

[22] Filed: Nov. 21, 1990

Related U.S. Application Data

[63] Continuation-in-part of Ser. No. 357,045, May 24, 1990, abandoned, which is a continuation-in-part of Ser. No. 353,910, May 18, 1989, Pat. No. 4,959,324, which is a continuation-in-part of Ser. No. 195,881, May 19, 1988, Pat. No. 4,999,287, and a continuation-in-part of Ser. No. 64,883, Jun. 22, 1987, Pat. No. 4,973,549.

[51] Int. Cl.$^5$ .......................... C12Q 1/60; C12Q 1/26; C12Q 1/28; G01N 21/00
[52] U.S. Cl. ................................. 435/11; 422/56; 435/25; 435/28; 436/71; 436/169; 436/170
[58] Field of Search ...................... 435/11, 19, 25, 28; 436/71, 824, 169, 170; 422/561

[56] References Cited

U.S. PATENT DOCUMENTS 4,959,324 9/1990 Ramel et al. ..................... 436/169

Primary Examiner—Michael G. Wityshyn
Assistant Examiner—Ralph Gitomer
Attorney, Agent, or Firm—Bertram I. Rowland

[57] ABSTRACT

High density lipoprotein-cholesterol determination is made employing a device which allows for removal of red blood cells, measurement of sample volume, removal of LDL and VLDL, and quantitation of HDL-cholesterol on a quantitation strip.

17 Claims, 2 Drawing Sheets

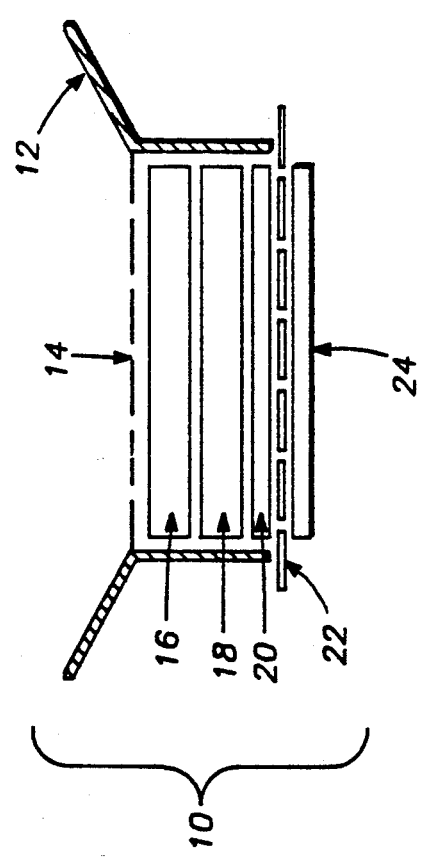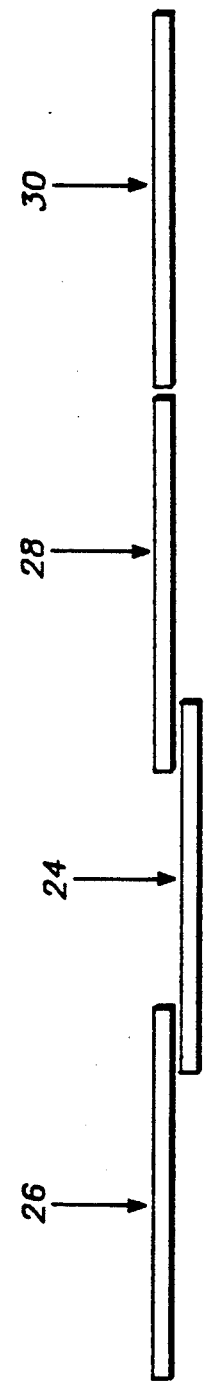
FIG.—1A
FIG.—1B

HDL DETERMINATION IN WHOLE BLOOD

CROSS-REFERENCE TO RELATED APPLICATIONS

This application is a continuation-in-part of application Ser. No. 357,045 filed May 24, 1990, now abandoned, which is a continuation-in-part of application Ser. No. 353,910, filed May 18, 1989 now U.S. Pat. No. 4,959,324, which in turn was a continuation-in-part of application Ser. No. 195,881 filed May 19, 1988, now U.S. Pat. Nos. 4,999,287, and 64,883 Jun. 22, 1987, now U.S. Pat. No. 4,973,549.

INTRODUCTION

1. Technical Field

The field of this invention is noninstrumented quantitative determination of high-density lipoprotein-cholesterol in whole blood.

2. Background

High-density lipoprotein (HDL) consists of a number of heterogeneous particles that vary with respect to size, content of lipid, and apolipoprotein. The major apolipoproteins found in HDL are A(I) and A(II) and these proteins constitute about 90% of total HDL protein. The roles of HDL in lipid transport are (1) to act as a reservoir of C apoprotein required for triglyceride transport; (2) to act as a "scavenger" of surplus cholesterol and phospholipids liberated from lipolysed triglyceride-rich lipoproteins; and (3) to transport surplus cholesterol from peripheral tissues to the liver for excretion and catabolism, both directly and indirectly, via other lipoproteins and the lipid transfer proteins.

HDL concentration has been found to correlate inversely with coronary heart disease. Epidemiologic studies have emphasized the importance of HDL as a negative risk factor. There is, therefore, substantial demand for an easy method for quantitation of this lipoprotein. Currently, the determination of HDL-cholesterol is extremely difficult and impractical to quantitate directly. The primary methods depend on the measurement of the plasma content of HDL-cholesterol after selective separation. Several methods are available for separation, such as ultra-centrifugation, electrophoresis, precipitation as in soluble complexes between lipoproteins, polyanions and divalent cations, gel or membrane filtration; and precipitation with antibodies to the apolipoproteins.

Ultracentrifugation, followed by precipitation with heparin and manganese chloride is the most commonly used reference method. Ultracentrifugation separates VLDL on the basis of differential density, while heparin-manganese chloride removes LDL by precipitation. HDL is estimated as cholesterol in the plasma fraction of a density greater than 1.063 g/ml. Ultra-centrifugation requires expensive instrumentation and significant technical skill and has therefore found limited application. Electrophoretic techniques lack precision and accuracy in the range of 20-40 mg/dL, where the greatest clinical interest lies. Gelpermeation chromatography is too complex and time consuming for routine analysis. There is, therefore, a clear interest in the development of techniques having relatively simple protocols and equipment for the quantitative determination of cholesterol in high-density lipoprotein.

RELEVANT LITERATURE

See also Allen, M. P., Delizza, A., Ramel, U., Jeong, H., and Singh, P. *A Non-instrumented Quantitative Test System and its Application for Determining Cholesterol Concentration in Whole Blood, Clin. Chem.* 1990; 36(9) 1591-1597; and Ramel, U., Allen, M. P., and Singh, P. *Sample Pad Assay Initiation Device and Method of Making* U.S. Pat. No. 4,959,324, issued Sep. 25, 1990.

SUMMARY OF THE INVENTION

High-density lipoprotein-cholesterol is quantitated from blood by removal of apoB containing lipoproteins with a membrane, followed by enzymatic reaction of cholesterol and cholesterol esters to produce hydrogen peroxide. The hydrogen peroxide is then quantitated on a quantitation strip to which a coupling dye is bound, which reacts with the product of the peroxidase to produce a detectable colored product.

BRIEF DESCRIPTION OF THE DRAWINGS

FIGS. 1a and 1b are diagrammatic side views of a separation device and the quantitation strips, respectively.

DESCRIPTION OF THE SPECIFIC EMBODIMENTS

Figure 2:
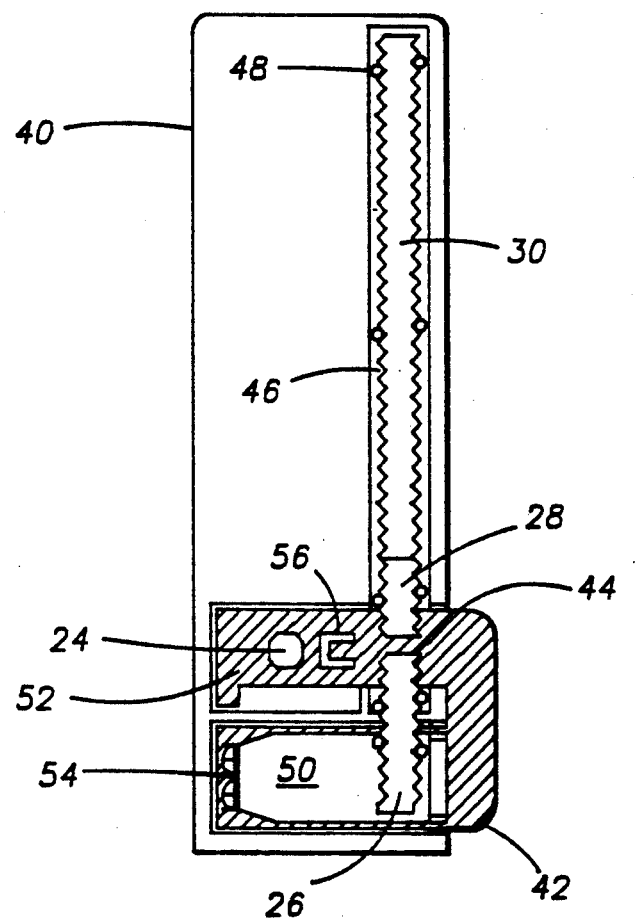
FIG. 2 is a diagrammatic plan view of a base plate and slide of an alternative quantitation device.

Method and devices are provided for the determination of high-density lipoprotein-cholesterol (HDL-cholesterol) from blood. The method and device provide for initial removal of a substantial proportion of the red blood cells present in the blood, removal of substantially all of the very low density lipoprotein (VLDL) and low density lipoprotein (LDL), which lipoproteins contain apo B lipoprotein. The resulting HDL-cholesterol concentrated plasma fraction is then treated with enzymes which react with cholesterol and cholesterol esters to produce hydrogen peroxide. Preferably, the hydrogen peroxide is then measured by transport of the hydrogen peroxide on a quantitation strip in conjunction with a peroxidase, where a compound is conjugated to the strip. The reaction of the peroxidase with a coupling compound results in the coupling compound reacting with another compound bound to the strip with production of a highly colored product. The distance of the colored front from the sample site or other designated position is quantitatively related to the amount of HDL-cholesterol in the blood sample.

A series of membranes are provided which allow for a number of functions in producing the desired sample, which is free of red blood cells and free of cholesterol associated with lipoproteins other than HDL. The first stage is the application of the blood sample to one or more membranes, desirably having diminishing pore size. The membranes are selected to efficiently remove red blood cells without lysis. Significant lysis of red blood cells results in the discoloration of the sample, which discoloration interferes with the measurement for the determination of HDL-cholesterol and more importantly hemoglobin may chemically interfere with the assay system. Generally, the pore size will be in the range of 0.5 to 50 $\mu$m, whereas with two filters, the first filter will have a pore size in the range of about 5 to 50 $\mu$m, while the second filter will have a pore size in the range of about 0.5 to 10 $\mu$m. The filters are selected to minimize the sample holdup in the filter and should substantially reduce the red blood cells (RBC) which are transferred to the next membrane layer.

The next membrane layer normally serves to remove VLDL and LDL, which include apolipoproteins B, C and E and various techniques may be employed for the removal of the cholesterol associated with VLDL and LDL. Alternatively one may use two treated glass fibre membranes for removal of LDL and VLDL at the same time as the RBC are being removed.

Another possibility is the use of either one or more filters (filter 1 and/or 2) to remove VLDL and LDL, while at the same time separating the red blood cells (see FIG. 1a).

In a preferred embodiment, a membrane comprising a divalent cation containing anionic polymer, which minimizes red blood cell lysis and efficiently separates the VLDL and LDL from the HDL, is employed. Illustrative of such polyanion products are dextran sulfate having magnesium as the counterion, or sodium heparin having divalent manganese as the counterion. Of particular interest, therefore, are polymers of at least about 5,000 molecular weight, usually at least about 50,000 molecular weight, particularly heparin (5–20 kDal) or dextran (25–500 kDal) which are sulfuric acid derivatives, sulfonates or sulfates, in conjunction with divalent cations, particularly magnesium and manganese. The polymers may be covalently or non-covalently bound to a porous substrate, so long as the polymers are retained by the porous substrate during the subject procedure. Various substrates may be employed, such as glass fiber, paper, synthetic membranes, or the like. The various substrates may be activated for covalent bonding by a variety of conventional agents, such as silane, e.g., aminopropyltriethoxysilane, with glass fiber, activated, e.g., carbodiimide-activated, paper or synthetic membranes, or the like. The amount of polymer bound to the membrane may be readily determined by determining the efficiency with which the HDL is separated from the VLDL and LDL and the loss of HDL on the membrane. The polymers may be bound to any or all of the porous filtration substrates. That is in a preferred embodiment, the VLDL and LDL precipitating reagent may be bound to polymeric membrane, filter 1, filter 2, membrane 3 or it may be bound to the sample receiving pad. The precipitating reagents may be bound onto any combinations of 2 or 3 or all porous substrates. (See FIG. 1)

Usually, the amount of polymer will be about 0.001 g to 0.5 g per $cm^2$. The membrane will generally have a thickness in the range of about 10 $\mu m$ to 1000 $\mu m$ and a pore size in the range of about 0.1 to 50 $\mu m$.

Instead of using precipitating reagents, affinity reagents may be employed, such as monoclonal or polyclonal antibodies specific for apolipoproteins B, C, and E. The use of the antibodies also allows the determination of LDL uncontaminated with HDL, by employing antibodies specific for the apo A protein on the LDL, which will allow passage of the HDL through the membrane.

The antibodies may be bound to the membranes described above by analogous techniques, using carbodiimide, cyanogen bromide, diazo compounds, activated olefins for reaction with thiol groups, or the like. The amount of antibodies bound to the membrane will vary with the affinity of the antibody, the number of active sites, the molecular weight of the antibody, e.g., IgM or IgG, or the like. Usually, the amount of antibody will be in the range of about 0.1 $\mu g$ to 100 $\mu g$ per $cm^2$. These antibodies may be immobilized on the polymeric membrane, filters 1 or 2 or membrane 3 or on the sample receiving pad (FIG. 1). The polymeric membrane may be positioned above, or in between filters 1 and 2, or membrane 3.

There may be one or more additional membranes to separate the sample receiving pad from the LDL removing membrane, to control flow, to further remove particulate matter, or for other purposes. These membranes will not be reactive, generally having pore sizes in the range of about 0.5 $\mu m$ to 1.0 $\mu m$.

Illustrative membranes which may find use for removal of red blood cells include S&S Glass 30, Whatman GFD, S&S 3662, Pall glass fiber membranes, Sartorius cellulose acetate, Filterite polysulfone asymmetric membrane, Ultrabind 450, Nucleopore, etc. Membranes which find use for removal of LDL are illustrated by Whatman GFD, Whatman 31ET or Ultrabind 450.

The sample is received by a sample pad. The sample pad may serve a number of functions. The sample pad, in conjunction with other components, may serve to measure the volume of the sample. The sample pad will usually have a volume of about 1 to 60 $\mu l$ and a thickness of about 0.1 to 5 mm. In addition, the sample pad may have one or more reactants, particularly enzyme reactants bound to the pad. The sample pad will initially be protected from contact with the quantitation strip. Various mechanisms may be employed to provide a barrier for contact between the sample pad and the quantitation strip, which barrier may be moved to allow for contact between the sample pad and the quantitation strip.

The sample pad may conveniently be a bibulous membrane, which will absorb the plasma sample and serve as a bridge for transport of eluent from an eluent source through the sample pad to conversion pad and subsequently to the quantitation strip and allow for substantially quantitative transport of cholesterol (including cholesterol precursors) or an enzymatic reaction product of cholesterol from the reaction pad to the quantitation strip.

While it is preferred that one or more of the membranes serve to remove VLDL and LDL, the reagent may be present solely on the sample pad, solely on the membrane for removing RBCs, combinations thereof, or on all or some of the components of the device in which the plasma contacts before undergoing substantial enzymatic reaction. Where the enzymes are on the pad, the reagent for removing the VLDL and LDL will not be restricted to the sample pad.

The cholesterol is measured by reaction with a combination of enzymes, cholesterol esterase and cholesterol oxidase. The esterase provides for hydrolysis of cholesterol esters to cholesterol, while cholesterol oxidase provides for oxidation of cholesterol with oxygen to hydrogen peroxide. The enzyme may be present on the pad, may be upstream from the pad in a reaction zone prior to the quantitation region of the quantitation strip, or a combination thereof. The enzymes may but are not required to be non-diffusively bound to the surface, so that the enzymes will substantially remain at the site where they are positioned prior to the beginning of the assay.

The sample pad may be protected from acting as a bridge and contacting the quantitation strip in a variety of ways. In one embodiment, a removable plastic barrier may be inserted between the sample pad, the quantitation strip, and the strip providing the source of eluent. The plastic barrier may include a mesh strip, e.g., Nitex ®, 100–500μ, for wiping the pad of excess sample. In another embodiment, the pad may be at a site distant from the quantitation strip and the eluent providing strip, where after receiving the sample, the sample pad is moved into contact with the two strips. In both of these cases, various wiping means may be employed to remove excess sample from the pad, so that a substantially reproducible amount of sample will be absorbed by the pad.

The eluent-supplying strip may be of any convenient bibulous material which can be dipped into an eluent and wick the eluent up to the sample pad, when the sample pad is in contact with the eluent source strip. Various papers may find use, such as cellulose strips, e.g., chromatography paper, silica on a support, alumina on a support, polymeric membranes, such as nitrocellulose and nylon. Generally, the eluent source strip will be not less than about 0.5 cm and not more than about 2.5 cm.

The quantitation strip may serve, as already indicated, in providing a reaction zone, where the cholesterol esters and enzymes are present which will react with the cholesterol to produce the reactant, hydrogen peroxide. Thus, a zone may be provided where the cholesterol will react to produce hydrogen peroxide, which will then be transported by the eluent to the quantitation region. The quantitation region is characterized by having one member of a dye couple bound to the region at a concentration which allows for a reasonable dynamic range associated with the concentration range of interest of HDL. For the most part, the concentration range of interest is from about 20 to 100 mg/dL of HDL-cholesterol, so that one wishes to have at least about 10 mm, per 25 mg/dL change in concentration, preferably at least about 7 mm per 25 mg/dL and not more than about 20 mm, usually not more than about 15 mm per 25 mg/dL.

The quantitation strip will generally have dimensions of about 5 mm to 130 mm and may be of the same or different material from the eluent source strip. Passively adsorbed to the strip will be one member of a dye couple, such as MBTH or AAP. The coupling member may be any of a variety of substrates for horseradish peroxidase, which can couple with the other member bound to the strip. Illustrative coupling members include N,N-dimethylaniline; 5-(N-methylanilino pentanoyl ethylene diamine; N-ethylaniline; N-ethylmeta-toluidine; 2-(N-ethyl-meta-toluidino)ethanol; N-ethyl-N-(2-hydroxy-3-sulfopropyl)-meta-toluidine sodium salt; N-ethyl, N-sulfopropyl-meta-toluidine sodium salt; 2-(N-ethyl-m-toluidino)ethanol, N-ethyl meta-toluidine; 1,8-dihydroxy-3,6-dimethoxynaphthalene or analogs thereof. These compounds are characterized by being capable of reacting in the presence of a peroxidase with hydrogen peroxide to form a compound which may be coupled with MBTH to form an indamine dye, which allows for detection of a color front in relation to the amount of hydrogen peroxide produced from the cholesterol in the sample.

The eluent will comprise the horseradish peroxidase, the coupling member, usually buffers, and other miscellaneous additives as appropriate, e.g., PVP, non-interfering proteins, detergents, particularly nonionic detergents, antifungal agents, etc. The concentration of the horseradish peroxidase will generally be in the range of about $0.29\mu$/ml to $1.6\mu$/ml, usually about 2–14 $\mu$g/ml. Buffers will generally provide a pH in the range of about 4 to 9, with a buffer concentration that will be sufficient to provide the necessary buffering, generally being in the range of about 10 to 500 mM. Illustrative buffers include phosphate, Tris, MOPSO, MOPS, borate, carbonate, etc.

In carrying out the assay, a blood sample may be placed on the topmost membrane and gravity and capillary action provide the transport force. The blood will migrate through the red blood cell separating membrane(s), so that the sample is substantially free of red blood cells when it contacts the membrane for removal of cholesterol present as other than HDL. The plasma sample will pass through the reactant membrane, so as to remove LDL and VLDL and leave HDL as the only protein-bound cholesterol. In a second embodiment the red blood cell separating membranes and the treated or reactant membranes, which removes VLDL and LDL, are the same. The sample receiving pad may also be used as a reactant membrane, The sample will then migrate to the sample pad and be absorbed by the sample pad. When the sample pad is at least saturated, the excess fluid will be removed as described above by moving the pad or other instrumentality, which serves to wipe the pad of the excess fluid. The pad will now be in contact with the eluent source strip and the quantitation strip. The eluent will move through the eluent source strip, using the pad as a bridge and carry cholesterol, cholesterol esters, and/or enzymatic products of cholesterol up to be quantitation region, where the hydrogen peroxide will react with the coupling agent to activate the coupling agent to react with the other member of the dye bound to the quantitation strip in the quantitation region. The extent of the color produced from an arbitrary point at the beginning of or prior to the quantitation region may be related to the amount of HDL-cholesterol in the sample. By using known standards, the distance of the color front from some origin, can be directly related to the amount of HDL-cholesterol in the sample in a quantitative manner.

Turning now to FIGS. 1a and 1b and 2, the subject invention will be further described. The separation device 10 of FIG. 1a has a well 12 in which is situated in the direction of flow, polymeric membrane 14, filter 1, 16, filter 2, 18 membrane 3, 20 and polycarbonate membrane 22. The separation and well sit over sample pad 24.

The polymeric membrane 14 serves to remove red blood cells without lysis, while filters 1 and 2, 16 and 18, respectively, are activated to remove VLDL and LDL, while allowing HDL to pass through. To further improve filtering, membrane 20 is provided to further ensure removal of VLDL and LDL, where membrane 3 may be activated in the same or different way from filters 1 and 2.

A polycarbonate membrane 22 serves to prevent contact between membrane 3, 20 and sample pad 24.

As depicted in FIG. 2 sample pad 24 is moved from a first position as shown in the FIG. 2 to a second position, as shown in FIG. 1b, where the sample pad 24 comes into contact with the conversion area 28 and wicking strip 26 to act as bridge to allow flow of fluid from the wicking strip 26 through the sample pad 24, conversion area 28, to the quantitation strip 30.

The sample on sample pad 24 is carried by wicking buffer from wicking strip 26 into conversion area 28 in which enzymes are present to convert cholesterol and cholesterol esters to hydrogen peroxide. The wicking buffer then carries the hydrogen peroxide into the quantitation area 30, where the hydrogen peroxide reacts with dyes under catalysis with by horseradish peroxidase. The extent of color formation is related to the amount of HDL present as indicated by the amount of cholesterol present in the HDL.

The measurement device may be fabricated from three injection molded parts or by any other convenient process. The parts comprise a base plate 40, a slide 42 and a clear cover plate, not shown. The base plate 40 consists of a cutout to accept the slide 42, a slot 46 with locating pins 48 into which the conversion area 28, quantitation strip 30 and wicking strip 26 are precisely positioned, maintaining about a 2 mm gap 44 between them, and a well 50 designed to capture the released transport solution, e.g., wicking buffer.

The slide 42 consists of a vented receptor site 52 into which the reagent 24 pad is inserted and over which the separation device 10 is placed. An arm 54 with dual shearing designed to facilitate the release of the transport solution from a pouch which is housed in a well of the cover plate, and a snap 56 to lock the slide in place, once pulled are provided. The cover plate consists of a well 32, which houses a sealed foil pouch (not shown) containing the transport solution. The cover plate has an orifice for placement of the separation device 10 for the introduction of the sample. The cover plate also comprises a squeegee metering bar which serves to control the volume of sample absorbed by the sample pad 24.

The following examples are offered by way of illustration and not by way of limitation.

EXPERIMENTAL

Experimental Details

Standard Curve

1. An assay is performed by using mylar laminated chromatography strips containing the quantitation region (70×5 mm), conversion region (7×5 mm), sample pad (7 ×5 mm) and wicking strip (12×5 mm). The wicking reagent is (0.1M) MOPSO buffered (pH 7.0) protein solution containing HRP (5 μg/ml). The paper employed for the quantitation region is 0.1 mg/ml MBTH paper and human serum samples equivalent to 25, 50, 75 and 100 mg/dL of HDL were employed.

The assay is carried out as follows:
(a) 0.01 ml of plasma or serum is deposited on the sample pad; (b) wicking is initiated by allowing the lower portion of the assay strip to contact 0.5 ml wicking reagent contained in a test tube. The assay is complete when the wicking solution reaches the end of the measurement region. The strips are then removed and the height to which the colored band is formed is plotted against cholesterol concentration. A substantially linear plot was obtained, with the migration height varying from about 15 mm to about 40 mm.

The assay was also performed with hydrogen peroxide calibrators equivalent to 25, 50, 75 and 100 mg/dL. The plot of migration height versus hydrogen peroxide incubation was substantially linear with migration height varying from about 22 mm to about 48 mm 2. Gel Electrophoresis AccuMeter ® cassettes A (FIG. 2) (see U.S. application Ser. No. 353,910 filed May 18, 1989, now U.S. Pat. No. 4,959,) with treated and untreated membranes are used for this study. Filters 1, 2, membrane 3 and/or a combination of 1, 2, 3 or all may be treated with the precipitating reagents.

The assay involves the application of whole blood or its plasma (0.04 ml) to the sample site on the cassette. Following a two minute incubation the sample pad is removed from the cassette and its plasma contents squeezed out (0.005 ml) and applied to an Agarose gel. After the last sample has been applied to the gel, 10 mins. are allowed for diffusion. The gel is placed into a Paragon electrophoresis cell and electrophoresed for 50 mins. at 100 volts. Upon completion of electrophoresis, the gel is removed from the Paragon electrophoresis cell and placed into a fixative solution for 5 mins.

The gel is removed from the fixative solution and dried until completely dry. The dried gel is processed in the following sequence:

| Lipoprotein working stain | 5 minutes |
| --- | --- |
| Destain Solution I | 3 dips |
| Destain Solution II | 3 dips |
| Destain Solution III | 5 minutes |

The gel is finally rinsed in a deionized water and then completely dried. Eight samples were electrophoresed: 1 whole blood (cassette with untreated membranes; 2 and 3 whole blood (cassette with treated membranes); 4 plasma (cassette with untreated membranes); 5 and 6 plasma (cassette with treated membranes); 7 and 8 supernatant of plasma following LDL and VLDL precipitation using phosphotungstate/$Mg^{2+}$. With the exception of sample 1 and 4, using untreated cassettes which showed the presence of pre-$\beta$ and $\beta$ subunits, all of the samples only showed the presence of the $\alpha$ subunit.

Cholesterol Analyses

Cholesterol concentrations are determined following in situ precipitation in AccuMeter ® cassettes (FIG. 2). AccuMeter cassettes with treated and untreated membranes are used for this study. Filters 1, 2, membrane 3 and/or a combination of 1, 2, 3 or all may be treated with the precipitating reagents. Boehringer Mannheim Diagnostic high performance reagent (BMDHP) is used to measure the plasma cholesterol collected on the sample pad. BMD Preciset aqueous based cholesterol calibrators equivalent to 50, 100, 150, 200, and 300 mg/dL are used for this study.

Whatman glass fibers GF/D(6.0 μm and/or Whatman 31ET chromatography paper were used to prepare treated membranes. The precipitating reagent solutions were prepared as follows: (1) Into deionized water (50 ml) was dissolved 0.5 g dextran sulfate (Na salt, Mw 500 kD), followed by the slow addition of 4.26 g anhydrous $MgCl_2$ with stirring, (2) Into 30 ml deionized water was dissolved 0.421 g heparin (Na salt, 176 USP units/mg) and 2.97 g $MnCl_2$.

The precipitating reagent (12 ml) was poured into a lasagne dish tilted at 45°. The membrane material (10 cm×7 cm) was slowly and uniformly passed through the reagent solution. (The GFD membrane was supported by Nitex nylon screen of the same dimension.) The membrane was then dried in an oven at 80° C. for about 15 min being inverted occasionally for uniformity. Discs (5 mm dia.) were then cut.

For solution phase precipitation, the dextran sulfate solution was prepared as described above, the heparin solution was twice as concentrated, and the phosphotungstate/$Mg^{2+}$ solution was prepared by diluting 4:1 BMD-HDL-cholesterol reagent (0.55M phosphotungstic acid; 25 mM $MgCl_2$) in deionized water.

The assay involves the application of plasma or serum (0.04 ml) to the sample site on the cassette. Following a two minute incubation, the slide is pulled and the sample receiving pad removed and placed in the BMDHP reagent (1 ml). The plasma or serum sample on the pad (0.005 ml) is extracted for one hour at room temperature. The solution is then measured at A500 nm. A standard curve is generated by pipetting BMD cholesterol calibrators (0.005 ml) into the BMDHP reagent (1 ml), incubating for 15 mins. and then measuring the absorbance at 500 nm.

LDL and VLDL precipitation was also performed in test tubes using the precipitating reagents and assay protocol listed below:

| Ppt Reagent | Ppt Reagent Vol. | Sample Vol. |
|---|---|---|
| Phosphotungstate/$MgCl_2$ (diluted 4:1 in $H_2O$) | 0.5 ml | 0.2 ml |
| Dextran $SO_4$/$MgCl_2$ | 0.05 ml | 0.5 ml |
| Heparin/$MnCl_2$ | 0.05 ml | 0.5 ml |

I) Vortex to mix sample and incubate for 10 min at RT.
II) Centrifuge at 2000×g for 10 min at RT.
III) Remove supernatant for further analyses The supernatant was analyzed for cholesterol as shown for the cholesterol calibrators.

Results

| Sample | Cholesterol mg/dL | | |
|---|---|---|---|
| | Untreated Membrane | Treated Membrane 1 | Treated Membrane 2 |
| Whole Blood 1 | 170 (182.0) | 30.6 (68.0) | 54.5 (68.0) |
| Plasma 1 | 178 (182.0) | 31.5 (68) | 61.0 (68.0) |
| Plasma 2 | 129.9 (128.8) | 50.1 (52.1) | — |
| Plasma 3 | 193.4 (204.3) | 53.4 (45.1) | — |
| Plasma 4 | 267.3 (283.1) | 54.7 (84.7) | — |
| Plasma 5 | 176.5 (191.0) | 71.8 (56.0) | 71.2 (56.0) |

Key:
( ) Cholesterol concentrations as determined by a reference method in test tubes. Reference precipitation method used involves phosphotungstate/$Mg^{2+}$.
Treated membrane 1 = Dextran $SO_4$/$Mg^{2+}$
Treated membrane 2 = Heparin/$Mn^{2+}$ It is evident from the above results, that the subject methodology provides for a convenient, simple assay for HDL, so that one may be able to obtain both HDL-cholesterol and total cholesterol to have an appropriate evaluation of the risks for coronary heart disease and myocardial infarction. In addition, the methodology provides for substantially no measurements, washings, or other manipulative steps, other than providing a sample to the device. In this manner, untrained people or individuals interested in monitoring their cholesterol are able to make the necessary determinations.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of determining the amount of high density lipoprotein-cholesterol ("HDL-cholesterol") in a blood sample, said method comprising:
    passing a blood sample through a first membrane to remove substantially all red blood cells without significant lysis of said red blood cells to provide plasma free of red blood cells and red blood cell components at an assay determination interfering level;
    passing said plasma through a membrane system comprising at least one porous filtration membrane;
    collecting and measuring said plasma on a sample pad;
    bringing said sample pad in fluid transferring relationship with an eluent source strip and a quantitation strip, wherein at least one of said sample pad and a region of said quantitation strip proximal to said sample pad comprises non-diffusibly bound cholesterol esterase and cholesterol oxidase, wherein said quantitation strip comprises a dye forming compound capable of reacting with an oxidized coupling compound to produce an intensely colored dye evenly distributed along said quantitation strip downstream from said cholesterol esterase and cholesterol oxidase;
    eluting said sample and any enzymatic reaction product with an eluent comprising a peroxidase and said coupling compound, by contacting said eluent source strip with said eluent;
    wherein a reagent for selectively removing very low density and low density lipoprotein is bound to at least one of said first membrane, a membrane of said membrane system or said sample pad, while allowing said HDL-chlolesterol to substantially quantitatively pass through said second membrane whereby any cholesterol in said blood is oxidized to hydrogen peroxide and said coupling compound is enzymatically oxidized to couple with said dye forming compound to form a colored region along said quantitation strip of a length proportional to the amount of HDL-cholesterol in said blood.

2. A method according to claim 1, wherein said membrane system comprises dextran sulfate or heparin with a divalent cation salt wherein said cation is magnesium or manganese.

3. A method according to claim 2, wherein said divalent cation salt is manganese chloride.

4. A method according to claim 2, wherein said divalent cation salt is manganese chloride together with heparin.

5. A method according to claim 1, wherein said membrane system comprises antibodies to very low density lipoprotein and low density lipoprotein.

6. A method according to claim 5, wherein said antibodies comprise antibodies to apolipoprotein B.

7. A method according to claim 1, wherein said region of said quantitation strip proximal to said sample pad comprises said cholesterol esterase and cholesterol oxidase.

8. A method of determining the amount of high density lipoprotein-cholesterol ("HDL-cholesterol") in a blood sample, said method comprising:
    passing a blood sample through a first membrane to remove substantially all red blood cells without significant lysis of said red blood cells to provide plasma free of red blood cells and red blood cell components at an assay determination interfering level;

passing said plasma through a second membrane comprising a reagent for selectively removing very low density and low density lipoprotein, while allowing said HDL-cholesterol to substantially quantitatively pass through said second membrane;

collecting and measuring said plasma on a sample pad;

bringing said sample pad in fluid transferring relationship with an eluent source strip and a quantitation strip by removing a barrier between said sample pad and said strips while wiping said pad free of excess plasma, wherein at least one of said sample pad and a region of said quantitation strip proximal to said sample pad comprises non-diffusibly bound cholesterol esterase and cholesterol oxidase, wherein said quantitation strip comprises a dye forming compound capable of reacting with an oxidized coupling compound to produce an intensely colored dye evenly distributed along said quantitation strip downstream from said cholesterol esterase and cholesterol oxidase;

eluting said sample and any enzymatic reaction product with an eluent comprising a peroxidase and said coupling compound, by contacting said eluent source strip with said eluent;

whereby any cholesterol in said blood is oxidized to hydrogen peroxide and said coupling compound is enzymatically oxidized to couple with said dye forming compound to form a colored region along said quantitation strip of a length proportional to the amount of HDL-cholesterol in said blood.

9. A method according to claim 8, wherein said second membrane comprises dextran sulfate or heparin with a divalent cation salt, wherein said cation is magnesium or manganese.

10. A method according to claim 8, wherein said second membrane comprises antibodies to very low density lipoprotein and low density lipoprotein.

11. A method of determining the amount of high density lipoprotein-cholesterol ("HDL-cholesterol") in a blood sample, said method comprising:

passing a blood sample through a first membrane to remove substantially all red blood cells without significant lysis of said red blood cells to provide plasma free of red blood cells and red blood cell components at an assay determination interfering level;

passing said plasma through a second membrane comprising a reagent for selectively removing very low density and low density lipoprotein, while allowing said HDL-cholesterol to substantially quantitatively pass through said second membrane;

collecting and measuring said plasma on a sample pad;

bringing said sample pad in fluid transferring relationship with an eluent source strip and a quantitation strip by moving said sample pad from a first site to a second site to be in contact with said strips while wiping said pad free of excess plasma, wherein at least one of said sample pad and a region of said quantitation strip proximal to said sample pad comprise nondiffusibly bound cholesterol esterase and cholesterol oxidase, wherein said quantitation strip comprises a dye forming compound capable of reacting with an oxidized coupling compound to produce an intensely colored dye evenly distributed along said quantitation strip downstream from said cholesterol esterase and cholesterol oxidase;

eluting said sample and any enzymatic reaction product with an eluent comprising a peroxidase and said coupling compound, by contacting said eluent source strip with said eluent;

whereby any cholesterol in said blood is oxidized to hydrogen peroxide and said coupling compound is enzymatically oxidized to couple with said dye forming compound to form a colored region along said quantitation strip of a length proportional to the amount of HDL-cholesterol in said blood.

12. A method according to claim 11, wherein saids second membrane comprises dextran sulfate or heparin with a divalent cation salt, wherein said cation is magnesium or manganese.

13. A method according to claim 11, wherein said second membrane comprises antibodies to very low density lipoprotein and low density lipoprotein.

14. A device for measuring high density lipoprotein-cholesterol ("HDL-cholesterol") in blood, said device comprising:

a filtering and metering device comprising:

a coarse first filter to remove from about 10 to 90% of the red blood cells in a blood sample without significant lysis of said red blood cells;

a fine second filter to remove substantially all of the remaining red blood cells in said sample without significant lysis to provide a plasma sample wherein said lysis is less than an assay determination interfering amount;

a membrane for specifically removing very low density and low density lipoprotein;

a sample pad for receiving said plasma sample from said membrane;

means for removing excess plasma from said sample pad; and an assay device comprising:

a bibulous membrane support film;

first and second bibulous members supported by said support film in tandem separated juxtaposition along their axes;

means for bringing said sample pad into fluid transferring relationship with said first and second bibulous members to provide a fluid transferring bridge;

at least one of said sample pad and a region of said second bibulous member comprising cholesterol esterase and cholesterol oxidase, wherein said region is proximal to said sample pad, said second bibulous member further comprising a dye forming compound capable of reacting with an oxidized coupling compound to produce an intensely colored dye substantially evenly distributed along said second bibulous member downstream from said sample pad and region.

15. A device according to claim 14, wherein said membrane comprises a polymeric sulfuric acid derivative divalent cation salt.

16. A device according to claim 14, wherein said membrane comprises antibodies to very low density lipoprotein and low density lipoprotein.

17. A method of determining the amount of high density lipoprotein-cholesterol ("HDL-cholesterol") in a blood sample, said method comprising:

passing a blood sample through a first membrane to remove substantially all red blood cells without significant lysis of said red blood cells to provide plasma substantially free of red blood cells and red blood cell components, wherein said removal of red blood cells and lysis is to a level below an assay determination interfering level;

passing said plasma through a membrane system comprising at least one porous filtration membrane and a reagent for selectively removing very low density and low density lipoprotein, while allowing said HDL-cholesterol to substantially quantitatively pass through said second membrane; wherein said reagent may be bound to any membrane of said membrane system;

collecting and measuring said plasma on a sample pad;

bringing said sample pad in fluid transferring relationship with an eluent source strip and a quantitation strip, wherein at least one of said sample pad and a region of said quantitation strip proximal to said sample pad comprise non-diffusibly bound cholesterol esterase and cholesterol oxidase, wherein said quantitation strip comprises a dye forming compound capable of reacting with an oxidized coupling compound to produce an intensely colored dye substantially evenly distributed along said quantitation strip downstream from said cholesterol esterase and cholesterol oxidase;

eluting said sample and any enzymatic reaction product with an eluent comprising a peroxidase and said coupling compound, by contacting said eluent source strip with said eluent;

wherein a reagent for selectively removing very low density and low density lipoprotein, while allowing said HDL-cholesterol to substantially quantitatively pass through, is bound to said at least one membrane;

whereby any cholesterol in said blood is oxidized to hydrogen peroxide and said coupling compound is enzymatically oxidized to coupled with said dye forming compound to form a colored region along said quantitation strip of a length proportional to the amount of HDL-cholesterol in said blood.

* * * * *